United States Patent
Locke et al.

(10) Patent No.: US 8,905,983 B2
(45) Date of Patent: Dec. 9, 2014

(54) SYSTEM AND METHOD FOR UTILIZING EXUDATE WITH A REDUCED PRESSURE TREATMENT SYSTEM TO GENERATE ELECTRICITY

(75) Inventors: Christopher Brian Locke, Bournemouth (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 344 days.

(21) Appl. No.: 13/090,775

(22) Filed: Apr. 20, 2011

(65) Prior Publication Data
US 2011/0264062 A1    Oct. 27, 2011

Related U.S. Application Data

(60) Provisional application No. 61/326,924, filed on Apr. 22, 2010.

(51) Int. Cl.
| | |
|---|---|
| *A01M 1/00* | (2006.01) |
| *H01M 8/06* | (2006.01) |
| *H01M 16/00* | (2006.01) |
| *H01M 8/16* | (2006.01) |
| *H01M 8/04* | (2006.01) |
| *H01M 8/24* | (2006.01) |

(52) U.S. Cl.
CPC ............... *H01M 8/16* (2013.01); *Y02E 60/527* (2013.01); *H01M 16/006* (2013.01); *H01M 8/04082* (2013.01); *H01M 8/2475* (2013.01); *A61M 2205/82* (2013.01); *A61M 2205/8268* (2013.01)
USPC .......................................... 604/313; 429/422

(58) Field of Classification Search
USPC .............. 604/289, 319, 313, 317; 429/9, 400, 429/401, 416–418, 422, 443, 447, 452, 454, 429/498, 512, 513
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," *Current Problems in Modern Clinical Surgery:* Interdepartmental Collection, edited by V. Ye Volkov et al. (Chuvashia State University, Cheboksary, U.S.S.R. 1986);pp. 94-96 (certified translation).

(Continued)

*Primary Examiner* — Melanie Hand

(57) ABSTRACT

A method for providing reduced pressure treatment to a tissue site is further provided according to an illustrative embodiment. The method includes applying a reduced pressure to the tissue site. The method collects exudate drawn from the tissue site in a liquid collection chamber and utilizes the collected exudate in the liquid collection chamber to generate electricity.

23 Claims, 3 Drawing Sheets

(56) References Cited

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,160,637 B2 * | 1/2007 | Chiao et al. .................. 429/2 |
| 7,927,749 B2 * | 4/2011 | Swift et al. .................. 429/401 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0148913 A1 | 7/2005 | Weston |
| 2007/0048577 A1 * | 3/2007 | Ringeisen et al. ........... 429/30 |
| 2008/0286624 A1 | 11/2008 | Lovley et al. |
| 2009/0149821 A1 * | 6/2009 | Scherson et al. ............. 604/289 |
| 2009/0275884 A1 * | 11/2009 | McNulty et al. ............. 604/35 |
| 2010/0030132 A1 * | 2/2010 | Niezgoda et al. ............ 604/22 |
| 2010/0042074 A1 * | 2/2010 | Weston et al. ............... 604/543 |
| 2010/0125233 A1 * | 5/2010 | Edward S. et al. ........... 602/42 |
| 2010/0150991 A1 * | 6/2010 | Bernstein .................... 424/447 |
| 2011/0257573 A1 * | 10/2011 | Hong et al. .................. 602/46 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2008/049029 A2 | 4/2008 |
| WO | WO 2010/032038 A2 | 3/2010 |
| WO | WO 2010032038 A2 * | 3/2010 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

International Search Report for PCT International Application PCT/GB95/01983; Nov. 23, 1995.

(56) References Cited

OTHER PUBLICATIONS

PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Chariker, Mark E., M.D., et al; "Effective Management of incisional and cutaneous fistulae with closed suction wound drainage"; Contemporary Surgery, vol. 34, Jun. 1989, pp. 59-63.
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A.C. ® Therapy Clinical Guidelines: A Reference Source for Clinicians (Jul. 2007).
International Search Report and Written Opinion date mailed Aug. 24, 2011; PCT International Application No. PCT/US2011/033546.

\* cited by examiner

SYSTEM AND METHOD FOR UTILIZING EXUDATE WITH A REDUCED PRESSURE TREATMENT SYSTEM TO GENERATE ELECTRICITY

CROSS-REFERENCE TO RELATED APPLICATIONS

This application claims the benefit of U.S. Provisional Application No. 61/326,924, filed Apr. 22, 2010, which is hereby incorporated by reference.

BACKGROUND

1. Field of the Invention

The present invention relates generally to tissue treatment systems and in particular to systems and methods for collecting exudates.

2. Description of Related Art

Clinical studies and practice have shown that providing a reduced pressure in proximity to a tissue site augments and accelerates the growth of new tissue at the tissue site The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment. Fluids or exudates are generally collected in a canister for disposal or analysis.

The reduced pressure is typically applied by a reduced pressure source that may be a vacuum pump driven by a motor or other device. The reduced pressure source may be housed within a reduced pressure treatment unit which may contain other electrical devices including, for example, sensors, alarms, computers and processing units. All of this electrical equipment requires a separate source of electrical power.

SUMMARY

The problems presented by existing collection canisters are solved by the systems and methods of the illustrative embodiments described herein. In one illustrative embodiment, a method for providing reduced pressure treatment to a tissue site is provided. The method includes applying a reduced pressure to the tissue site. The method collects exudate drawn from the tissue site in a liquid collection chamber and utilizes the collected exudate in the liquid collection chamber to generate electricity.

In another illustrative embodiment, a reduced pressure treatment system for applying reduced pressure to a tissue site is provided. The reduced pressure treatment system includes a reduced pressure source for providing reduced pressure and a distribution manifold fluidly coupled to the reduced pressure source for receiving reduce pressure. The distribution manifold is adapted to be positioned at the tissue site to distribute the reduced pressure from the reduced pressure source. An energy production device is fluidly connected between the distribution manifold and the reduced pressure source for receiving exudate drawn from the tissue site in response to the reduced pressure. The energy production device contains a catalyst for generating electricity using the exudate.

In still another illustrative embodiment, an energy production device for collecting liquids from a tissue site in response to application of a reduced pressure to the tissue is provided for use with a reduced pressure treatment system. The energy production device includes an anode chamber having an anode adapted to transfer electrons from the anode chamber. The anode chamber is fluidly coupled between a source of reduced pressure and a distribution manifold at the tissue site to draw liquid including exudates from the tissue site into the anode chamber. The anode chamber contains micro-organisms for consuming a substrate within the exudate to produce carbon dioxide, protons, and electrons. The energy production device further includes a cathode chamber having a cathode adapted to receive the electrons from the anode. The cathode chamber has an electron acceptor capable of accepting electrons from the cathode. In addition, the energy production device includes a proton exchange membrane positioned between the anode and the cathode to enable passage of protons from the anode chamber to the cathode chamber. An output is electrically coupled to the anode to the cathode for providing energy to an electrical load in response to the microbial production of energy using the collected exudates from the tissue site.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
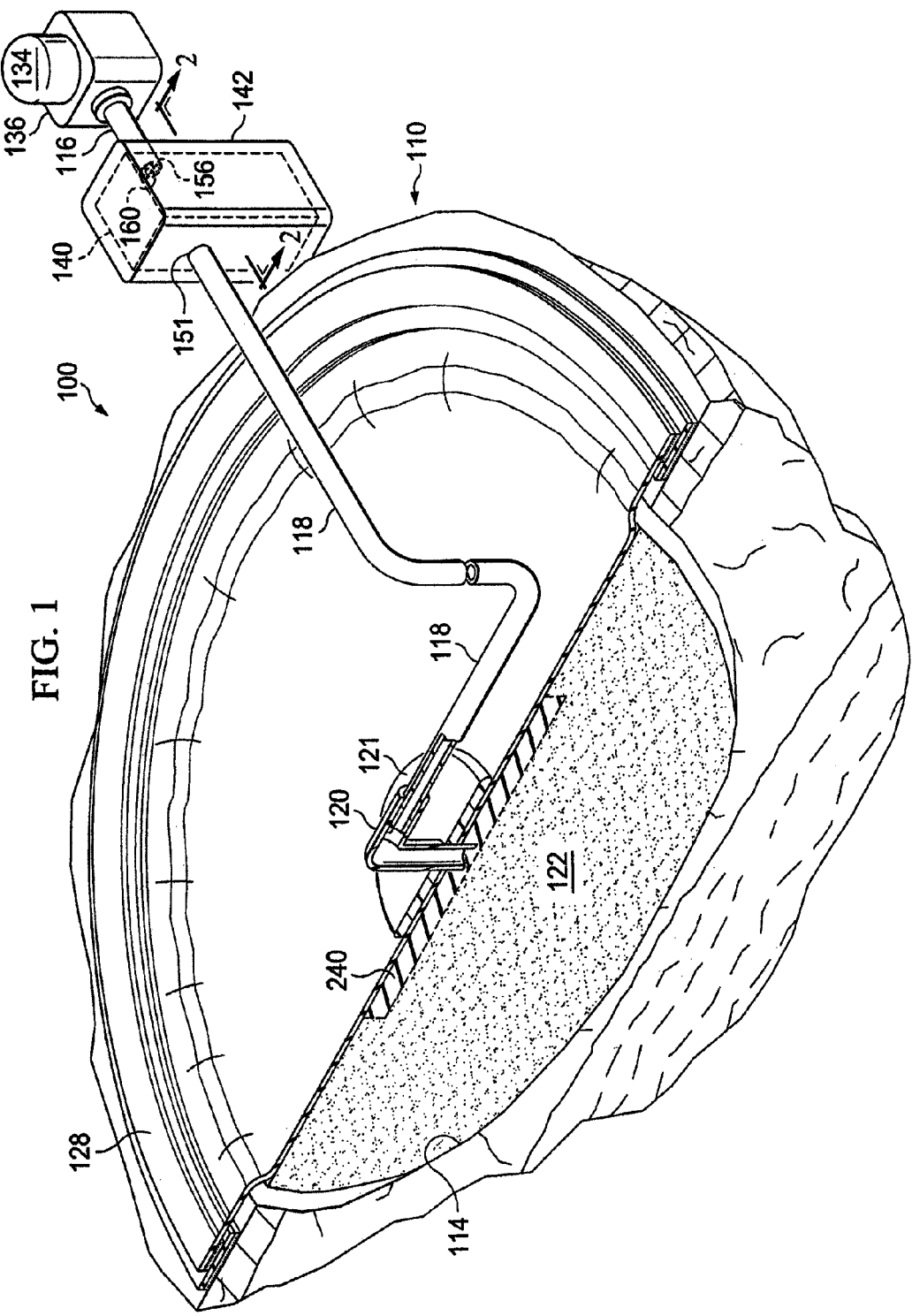
FIG. 1 illustrates a perspective, schematic view of a reduced pressure treatment system having a collection canister according to an illustrative embodiment.

Referring to FIG. 1, a reduced pressure treatment system 100 according to an embodiment of the invention comprises a dressing assembly 110 positioned over a tissue site 114 and a reduced-pressure source 134 for providing a reduced pressure to the dressing assembly 110. The system 100 further comprises a canister 142 that is coupled in fluid communication with the reduced-pressure source 134 via a conduit 116. The canister 142 is also in fluid communication with the dressing assembly 110 via a second conduit 118 and a tubing adapter 120. The canister 142 may be a fluid reservoir, or collection member, that filters or collects exudates and other fluids removed from the tissue site 114. As used herein, the term "coupled" includes direct coupling or indirect coupling via separate object. The term "coupled" also encompasses two or more components that are continuous with one another by virtue of each of the components being formed from the same piece of material. Also, the term "coupled" may include chemical, mechanical, thermal, or electrical coupling. Fluid coupling means that fluid is in communication with the designated parts or locations.

In one embodiment, the second conduit 118 may fluidly communicate with the tissue site 114 through a distribution manifold 122. The distribution manifold 122 may be any material, either bioabsorbable or non-bioabsorbable, that is capable of manifolding a reduced pressure to the tissue site 114. In certain embodiments, the distribution manifold 122 may be an open-cell, reticulated polyurethane foam. In other embodiments the distribution manifold 122 may function as a scaffold to support tissue growth or regeneration within the tissue site 114. A drape 128 may be placed over the distribution manifold 122 and sealed around a perimeter of the tissue site 114 to maintain reduced pressure at the tissue site 114.

The tubing adapter 120 provides an interface between conduit 118 and the reduced pressure dressing 300. In particular, the tubing adapter 120 fluidly communicates with the conduit 118 such that the conduit 118 transfers reduced pressure to the reduced pressure dressing 300 and the tissue site 114 via the tubing adapter 120. The tubing adapter 120 may be a conventional connector pad that is adapted to abut or be partially disposed within the aperture 360. Alternatively, the tubing adapter 120 may have a low profile dome shape, or the tubing adapter 120 may be any other shape. The low profile of the tubing adapter 120 may help to keep the reduced pressure dressing 300 compact and convenient for use by a user. The tubing adapter 120 includes a flange 121, which is disposed around the periphery of the tubing adapter 120 to provide a seal with the upper surface of the drape 128.

In one implementation, the reduced pressure source 134 may be a reduced pressure or vacuum pump driven by a motor. In another embodiment, the reduced pressure source may be a manually-actuated pump such as a compressible bellows pump. In still another embodiment, the reduced pressure source 134 may be a wall suction port such as are available in hospitals and other medical facilities. In yet another embodiment, the reduced pressure source 134 may be a piezoelectric disc pump that may be an integral component of the canister 142.

The reduced pressure source 134 may be housed within a reduced pressure treatment unit 136, which may also contain sensors, processing units, alarm indicators, memory, databases, software, display units, and user interfaces that further facilitate the application of reduced pressure treatment to the tissue site 114. In one example, a sensor (not shown) may be disposed at or near the reduced pressure source 134 to determine a source pressure generated by the reduced pressure source 134. The sensor may communicate with a processing unit that monitors and controls the reduced pressure that is delivered by the reduced pressure source 134. Delivery of reduced pressure to the tissue site encourages new tissue growth by maintaining drainage of exudate from the tissue site, increasing blood flow to tissues surrounding the tissue site, and by compressing the distribution manifold into the tissue site, thereby creating microstrain at the tissue site which stimulates new tissue growth.

Figure 2:
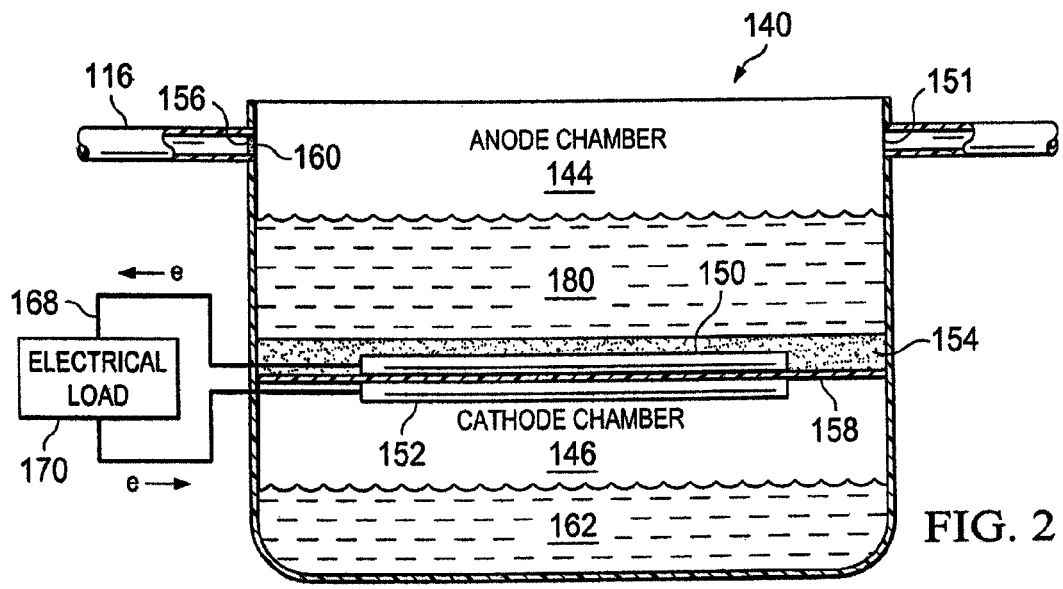
FIG. 2 illustrates a cross-sectional side view of the canister of FIG. 1 taken on the line 2-2.

Referring to FIGS. 1 and 2, one embodiment of the canister 142 includes an inlet 151 that is fluidly coupled to the conduit 118, and an outlet 156 that is fluidly coupled to the reduced pressure source 134. The outlet 156 includes a liquid-air separator 160 that is positioned within the first conduit 116 or simply covers the outlet 156 to prevent liquid from exiting the canister 142 through the outlet 156. Although the liquid-air separator 160 is hydrophobic, it does not restrict the flow of gaseous fluids so that the canister 142 is in fluid (gaseous) communication with the reduced pressure source 134 to maintain reduced pressure within the canister 142. The reduced pressure is provided to the tissue site 114 through the inlet 151, the conduit 118, the tubing adapter 120, and the distribution manifold 122. The reduced pressure draws exudate and other fluids from the tissue site 114 into the canister 142. The liquid-air separator 160 prevents liquids that that are drawn into the canister 142 from exiting the canister 142 through the outlet 156 and contaminating the reduced pressure source 134.

In an illustrative embodiment, the liquid-air separator 160 may be a hydrophobic filter that prevents passage of liquids through the outlet 156. Alternatively, the liquid-air separator 160 may be a gravity-based barrier system, or a device that includes a hydrophilic surface to encourage condensation or other separation of liquid from a fluid stream when the fluid stream passes over the surface. The hydrophobic surface is optimized to maximize dry air flow while maintaining acceptable fluid blockage, permitting small size and minimizing cost. Other examples of liquid-air separators 160 may include sintered metals, sintered nylons, or any other material or device that is capable of separating liquid from a fluid stream, or that is otherwise capable of preventing the passage of liquid while allowing the passage of gases.

In accordance with one embodiment, the canister 142 may comprise an energy producing component 140 that generates electricity using exudate collected from the tissue site 114. In one embodiment, the energy producing component 140 is a microbial fuel cell (MFC). A microbial fuel cell is an electrochemical device that employs the catalytic action of a microorganism such as bacteria to drive the oxidation of organic compounds. In some embodiments, the energy produced by the energy producing component 140 may be utilized to power one or more components of the reduced pressure treatment system 100.

Referring more specifically to FIG. 2, an illustrative embodiment of the energy producing component 140 is presented. In the depicted embodiment, the energy producing component 140 comprises an anode chamber 144, a cathode chamber 146, and a proton exchange membrane (the "PEM") 158 separating the anode chamber 144 and the cathode chamber 146. In certain embodiments, the anode chamber 144 serves as a primary reservoir for collecting exudates and other liquids from the tissue site 114 within the canister 142. The anode chamber 144 is subjected to the reduced pressure provided by the reduced pressure source 134 which draws exudate 180 from the tissue site 114 into the anode chamber 144 via the inlet 151.

The anode chamber 144 may contain an anolyte containing a plurality of micro-organisms for consuming the exudate in the anode chamber 144. Under anaerobic conditions, the micro-organisms extract and oxidize glucose from the exudate 180 to produce carbon dioxide, hydrogen protons, and electrons, as indicated in the following chemical equation: $C_{12}H_{22}O_{11} + 13H_2O \rightarrow 12CO_2 + 48H^+ + 48e^-$. As referenced herein, the term proton is used as a synonym for a positive hydrogen ion (H+). In one embodiment, the reduced pressure source 134 may be used to assist in removing oxygen, if any, in the anode chamber 144 for creating or maintaining anaerobic conditions in the anode chamber 144. In other embodiments, anaerobic conditions in the anode chamber 144 may be created or maintained with the use of an anaerobic gas pack (not shown) that absorbs oxygen in the anode chamber 144. In an exemplary embodiment, the generated carbon dioxide is released and exits out of the outlet 156 of the canister 142, while the generated electrons are utilized to produce electricity.

The anode chamber 144 includes a microbial layer 154 disposed on the PEM 158 and covered by the exudate 180, and further includes an anode 150 disposed adjacent the PEM 158 within the microbial layer 154. The microbial layer 154 contains inorganic mediators that tap into the electron transport chain of cells to liberate electrons from the electron transport chain. Examples of mediators that may be used include natural red, methyl blue, thionine, or resorfuin. The electrons gained from the oxidation of glucose within the exudate are transferred towards the anode 150. The cathode chamber 146 includes a cathode 152 disposed adjacent the PEM 158 which separates the cathode 152 from the anode 150. The PEM 158 may be comprised of ionomers and may be formed from either pure polymer membranes or from composite membranes. One of the most common and commercially available PEM materials is Nafion®, a DuPont® product. The PEM 158 functions so as to allow passage of only protons between the anode 150 and the cathode 152 from the anode chamber 144 to the cathode chamber 146. The anode 150 and the cathode 152 are electrically coupled via an electrical circuit 168 to an electrical load 170.

Electron flow from the anode 150 (negatively charged electrode) generates electrical power for the electrical load 170 as electrons transfer from the cathode 152 to a higher potential electron acceptor such as oxygen contained within the cathode chamber 146. The cathode chamber 146 receives the hydrogen protons produced from the oxidation of glucose that passes through the proton exchange membrane 158. Electrons and protons combine with the available oxygen in the cathode chamber 146 to form water 162 as a byproduct which collects within the cathode chamber 146 as shown. In some embodiments, aerobic conditions may be maintained in the cathode chamber 146 by enabling air to pass through the cathode chamber 146 through one or more openings in the cathode chamber 146 (not depicted in diagram). In such embodiments, the openings are covered with liquid-air separators (not shown) to prevent the water 162 from leaking out of the cathode chamber 146, but not restricting the flow of air. In other embodiments, the cathode chamber 146 may contain an oxidizing agent that combines with the electrons in the cathode chamber 146.

In addition, in certain embodiments, the cathode chamber 146 may include one or more openings (not depicted) for enabling removal of the water 162 generated by this process. In some embodiments, the energy producing component 140 may evaporate the water 162 from the cathode chamber 146 using the heat generated by the above process or by using the temperature of the wound fluid to aid in the evaporation process. Additionally, in some embodiments, the cathode chamber 146 may include one or more absorbent/adsorbent material for capturing the water 162.

The electrical load 170 may be any device that requires power for operation. For example, in some embodiments, the electrical load 170 may be the reduced pressure source 134 and/or may be one or more sensors associated with the reduced pressure treatment system 100, such as, but not limited to, a pressure sensor for monitoring the reduced pressure being applied to the tissue site 114 or a pH sensor for determining the acidity of a solution. In some embodiments, the generated electricity may be utilized to recharge a battery of the reduced pressure treatment unit 136 and/or may be accumulated and stored for future use. Alternatively, the generated electricity may be utilized in conjunction with a second power source to power one or more components of the reduced pressure treatment system 100.

Although FIGS. 1 and 2 depict the inlet 151 and the outlet 156 on the sides of the canister 142, the position, shape, and general configuration of the inlet 151 and the outlet 156 may vary depending on the shape and configuration of the canister 142. For instance, in some embodiments, the inlet 151 and/or the outlet 156 may be positioned on the top of the canister 142, as opposed to being located on the sides of the canister 142. In addition, the size, shape, and configuration of the anode chamber 144 and the cathode chamber 146 may vary depending on a particular design of the canister 142.

Figure 3:
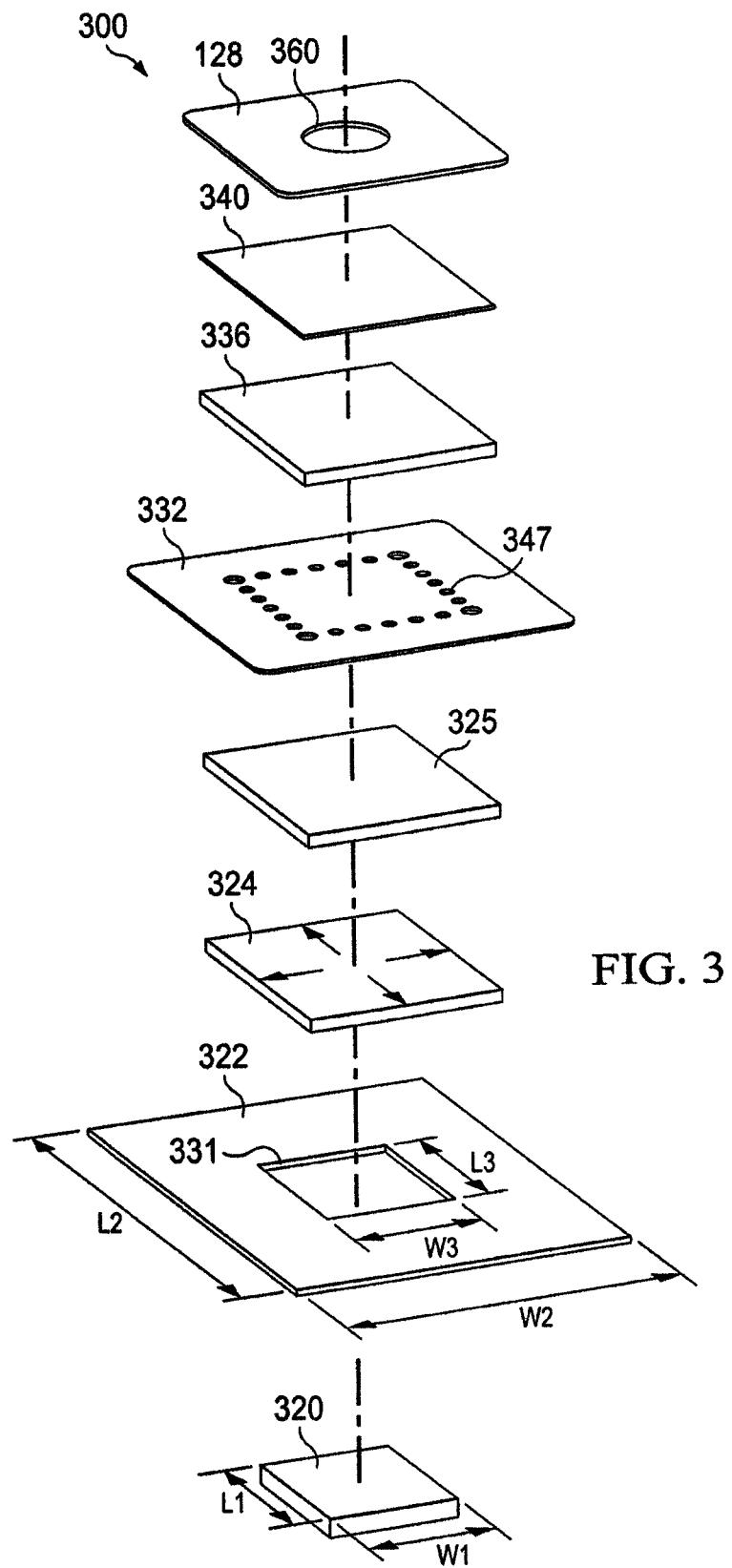
FIG. 3 illustrates an exploded perspective view of a dressing that incorporates a microbial fuel cell that may be utilized with a reduced pressure treatment system in accordance with an illustrative embodiment.

Another embodiment of an energy producing component 240 for a reduced pressure therapy system similar to the system 100 described above with reference to FIG. 1, may be integrated within dressing positioned adjacent the tissue site 114 as a component of the distribution manifold 122 or simply replacing the distribution manifold 122. The energy producing component 240 may be in addition to or in lieu of the energy producing component 140 contained within the canister 142. Referring to FIG. 3, an embodiment of such a reduced pressure dressing 300 is shown and, for example, may be used to replace the distribution manifold 122. The energy producing component 240 may be, for example, a microbial fuel cell (or "MFC") that comprises one of the layers of the dressing 300 that is disposed under the drape 128 in fluid communication with the reduced pressure source 134 as described above.

More specifically, the reduced pressure dressing 300 includes an interface layer 320 adapted to be positioned at the tissue site 114, and a seal layer 322 to seal the reduced pressure dressing 300 around the tissue site 114. A first manifold layer 324 is in fluid communication with the interface layer 320 to distribute the reduced pressure to the interface layer 320 and the tissue site 114. In one embodiment, a microbial fuel cell 325 is positioned in fluid communication with the first manifold layer 324 to collect exudate from at least one of the first manifold layer 324, the interface layer 320, and the tissue site 114. A diverter layer 332 is positioned adjacent the microbial fuel cell 325. A second manifold layer 336 is positioned in fluid communication with the diverter layer 332, and a liquid-air separator 340 is positioned adjacent the second manifold layer 336 under the drape 128.

The interface layer 320 of the reduced pressure dressing 300 is adapted to contact the tissue site 114. The interface layer 320 may be partially or fully in contact with the tissue site 114 being treated by the reduced pressure dressing 300. When the tissue site 114 is a wound, the interface layer 320 may partially or fully fill the wound. The interface layer 320 may be any size, shape, or thickness depending on a variety of factors, such as the type of treatment being implemented or the nature and size of the tissue site 114. For example, the size and shape of the interface layer 320 may be customized by a user to cover a particular portion of the tissue site 114, or to fill or partially fill the tissue site 114, as does the distribution manifold 122 of FIG. 1. Although the interface layer 320 illustrated in FIG. 3 has a square shape, the interface layer 320 may be shaped as a circle, oval, polygon, an irregular shape, or any other shape. The following description of the interface layer 320 applies equally to the distribution manifold 122.

In one illustrative embodiment, the interface layer 320 is a foam material that functions as a manifold to provide reduced pressure to the tissue site 114 when the interface layer 320 is in contact with or near the tissue site 114. The foam, material may be either hydrophobic or hydrophilic. In one non-limiting example, the interface layer 320 is an open-cell, reticulated polyurethane foam such as GranuFoam® dressing available from Kinetic Concepts, Inc. of San Antonio, Tex.

In the example in which the interface layer 320 is made from a hydrophilic material, the interface layer 320 also functions to wick fluid away from the tissue site 114, while continuing to provide reduced pressure to the tissue site 114 as a manifold. The wicking properties of the interface layer 320 draw fluid away from the tissue site 114 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The interface layer 320 may further promote granulation at the tissue site 114 when a reduced pressure is applied through the reduced pressure dressing 300. For example, any or all of the surfaces of the interface layer 320 may have an uneven, coarse, or jagged profile that causes microstrains and stresses at the tissue site 114 when reduced pressure is applied through the interface layer 320. These microstrains and stresses have been shown to increase new tissue growth.

In one embodiment, the interface layer 320 may be constructed from bioresorbable materials that do not have to be removed from a patient's body following use of the reduced pressure dressing 300. Suitable bioresorbable materials may include, without limitation, a polymeric blend of polylactic acid (PLA) and polyglycolic acid (PGA). The polymeric blend may also include without limitation polycarbonates, polyfumarates, and capralactones. The interface layer 320 may further serve as a scaffold for new cell-growth, or a scaffold material may be used in conjunction with the interface layer 320 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The seal layer 322 of the reduced pressure dressing 300 includes an opening or aperture 331 and provides a seal around the tissue site 114. The seal layer 322 may serve as a gasket around a portion of the tissue site 114 to prevent reduced pressure applied to the reduced pressure dressing 300 from leaking out of the reduced pressure dressing 300. The seal layer 322 may also be used to secure the interface layer 320 at the tissue site 114. If the drape 128 is wrinkled when applied to the healthy tissue surrounding the tissue site 114, then the seal layer 322 assists in maintaining the reduced pressure in the wrinkled portions.

The seal layer 322 may be any size and thickness capable of providing a seal around the tissue site 114. In the example of FIG. 3, a length, L2, and a width, W2, of the seal layer 322 are greater than a length, L1, and a width, W1, of the interface layer 320, respectively. Thus, portions of the seal layer 322 extend past the edges of the interface layer 320. These portions may contact the tissue surrounding the tissue site 114 directly, thereby providing a seal around the tissue site 114 and the interface layer 320. While the seal layer 322 has a square shape, the seal layer 322 may also have any other shape that provides a seal around the tissue site 114 or the interface layer 320. Non-limiting examples of other shapes include a circle, oval, any polygonal shape, an irregular shape, or a shape that is customized to contour to the tissue surrounding the tissue site 114 or the interface layer 320.

The seal layer 322 may be made from any material that is capable of sealing around the treated portion of the tissue site 114. In one illustrative embodiment, the seal layer 322 may include or be made from a hydrogel. The seal layer 322 may also include either or both of a hydrocolloid or silicon. Although the seal layer 322 is shown as being disposed adjacent to the interface layer 320, the seal layer 322 may be positioned adjacent or between any of the layers in the reduced pressure dressing 300.

The reduced pressure dressing 300 also includes a first manifold layer 324 for distributing the reduced pressure to and withdrawing or wicking liquid, such as exudate, from the interface layer 320. When the seal layer 322 is positioned adjacent the interface layer 320, liquid may be withdrawn from the tissue site 114 through the aperture 331. As a reduced pressure is applied to the reduced pressure dressing 300, the liquid is wicked from the tissue site 114 by the interface layer 320 and drawn through the aperture 331 of the seal layer 322 by the first manifold layer 324.

In one embodiment, a length, L3, and a width, W3, of the aperture 331 is less than the length, L1, and the width, W1, of the interface layer 320. However, in other embodiments, particularly in those embodiments in which one or more other layers are disposed between the seal layer 322 and the interface layer 320, the length, L3, and the width, W3, of the aperture 331 may be equal to or larger than the length, L1, and the width, W1, of the interface layer 320. While the aperture 331 illustrated in FIG. 3 has a square shape, the aperture 331 may instead have any other shape that allows the seal layer 322 to provide a seal while facilitating the passage of liquid from the tissue site 114. The first manifold layer 324 may have any size, shape, or thickness. For example, the size and shape of the first manifold layer 324 may also be customized based on the size and shape of other components in the reduced pressure dressing 300, such as the size and shape of the interface layer 320, the seal layer 322, the aperture 331, the microbial fuel cell 325, or other layers in the reduced pressure dressing 300.

The first manifold layer 324 is a biocompatible, porous material that is capable of distributing reduced pressure to the tissue site 114. The first manifold layer 324 may be made from foam, gauze, felted mat, or any other material suited to a particular biological application. The first manifold layer 324 includes a plurality of flow channels or pathways to facilitate distribution of reduced pressure or fluids to or from the tissue site 114. In one embodiment, the first manifold layer 324 is a porous foam and includes a plurality of interconnected cells or pores that act as flow channels. The porous foam may be a polyurethane, open-cell, reticulated foam such as GranuFoam® dressing. If an open-cell foam is used, the porosity may be about 400 to 600 microns or any other porosity capable of adequately manifolding reduced pressure. The flow channels allow fluid communication throughout the portion of first manifold layer 324 having open cells. The cells and flow channels may be uniform in shape and size, or may include patterned or random variations in shape and size. Variations in the shape and size of the cells of the first manifold layer 324 result in variations in the flow channels, and such characteristics may be used to alter the flow characteristics of fluid through first manifold layer 324. The first manifold layer 324 may be either hydrophobic or hydrophilic. In one embodiment, the first manifold layer 324 may be made from the same material as the interface layer 320.

In one embodiment, the first manifold layer 324 may be made from a material that expands upon contact with a liquid, such as exudate from the tissue site 114, so that the first manifold layer 324 collects the fluid and fills a portion of the tissue site 114. In this embodiment, the first manifold layer 324 may enable the interface layer 320 to be removed, thereby simplifying the construction and reducing the thickness or profile of the reduced pressure dressing 300.

Figure 4:
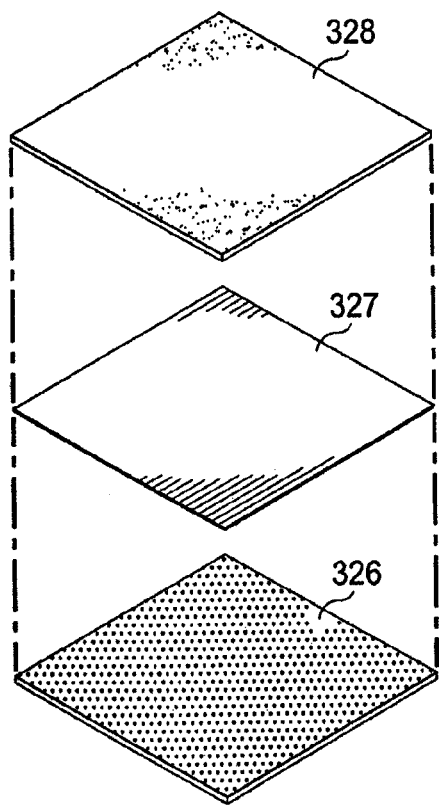
FIG. 4 illustrates an exploded perspective view of typical components of the microbial fuel cell of FIG. 3 in accordance with an illustrative embodiment.

Referring to FIGS. 3 and 4, the microbial fuel cell 325 comprises an anode chamber 326 and a cathode chamber 328 separated by a proton exchange membrane (a "PEM") 327, wherein the first manifold layer 324 and the anode chamber 326 may function similar to the anode chamber 144 as described above. The second manifold layer 336 and the cathode chamber 328 may function similar to the cathode chamber 146 as described above. In one embodiment, the anode chamber 326 includes microchannels (not shown) for receiving and collecting exudate distributed by the first manifold layer 324. The anode chamber 326 includes microorganisms for consuming glucose within the exudate to produce carbon dioxide, protons, and electrons. The size of the microchannels in the anode chamber 326 is advantageously selected such that the collection of exudate occurs without substantial risk of clogging. The microchannels surface may be coated with a conductor including, for example, Cr/Au as a current collector. In some embodiments, the anode chamber 326 may include an electron transfer mediator, such as, but not limited to, methyl blue for increasing the efficiency of electron transfer to the anode (not depicted). The electrons from the anode chamber 326 are transferred to an external electrical load (not depicted) for powering one or more components associated with the reduced pressure treatment system 100, while the protons passes through the PEM 327.

In one embodiment, the PEM 327 may be formed from a DuPont® Nafion® film for enabling only the passage of protons from the anode chamber 326 to the cathode chamber 328. However, in other embodiments, the PEM 327 may utilize any type of suitable material so as to allow passage of only protons from the anode chamber 326 to the cathode chamber 328. In one embodiment, the cathode chamber 328 contains an oxidizing material for accepting electrons from the cathode. For example, in one embodiment, ferricyanide ion $Fe(CN)_6^{3-}$ (typically in the form of potassium ferricyanide) can be used as an electron acceptor, becoming reduced to ferrocyanide $Fe(CN)_6^{4-}$. The ferrocyanide combines with the protons passed from the anode chamber 326 and produces water as a by-product. In one embodiment, the water may be stored in the cathode chamber 328. Alternatively, or in addition to, in some embodiments, the water is absorbed by the second manifold layer 336.

The reduced pressure dressing 300 may also include the diverter layer 332 disposed between the microbial fuel cell 325 and the second manifold layer 336. The diverter layer 332 includes a plurality of holes 347 though which reduced pressure from the reduced pressure source 134 (see FIG. 1) is applied. The reduced pressure is distributed to the diverter layer 332 by the second manifold layer 336. The holes 347 may be arranged in a pattern for applying the reduced pressure to certain areas of the microbial fuel cell 325 to enhance the capability of the microbial fuel cell 325 for collecting exudate from the tissue site 114. In the embodiment illustrated in FIG. 3, the plurality of holes 347 form a pattern around a peripheral portion of the diverter layer 332 away from the center of the diverter layer 332 so that the reduced pressure is applied to outer edges of the microbial fuel cell 325 which may contain fluid ports for collecting exudate into the anode chamber 326.

The diverter layer 332 may be made from any material that enhances the reduced pressure transmission and storage capabilities of an adjacent absorbent layer. For example, the diverter layer 332 may be made from a material that is substantially impermeable to liquid and gas. Alternatively, the material from which the diverter layer 332 is made may instead have a predetermined moisture vapor transfer rate that is consistent with gas permeability. In either example, the diverter layer 332 may still include a pattern of holes 347 for transmitting a greater volume of liquid or gas than that permitted by the gas-permeable material of which the diverter layer 332 is constructed. It should be noted, however, that permeability of the diverter layer 332 to gas but not liquid may result in increased transmission of reduced pressure through the dressing while still directing liquid flow around or near the perimeter of the diverter layer 332.

The diverter layer 332 has primarily been described as assisting in diverting reduced pressure or fluid flow to a perimeter region of the microbial fuel cell 325. Alternatively, the diverter layer 332 could instead be configured to assist in diverting reduced pressure to any particular region, i.e. a target region, of the microbial fuel cell 325 to enhance the collection of exudate from the tissue site 114.

Referring still to FIG. 3, the second manifold layer 336 distributes the reduced pressure more uniformly across the surface of the diverter layer 332. The second manifold layer 336 may be made from any material capable of distributing or manifolding fluid. In one example, the second manifold layer 336 may be made from a same or similar material as the first manifold layer 324. In this example, the second manifold layer 336 may include a plurality of interconnected cells that form a porous foam. The second manifold layer 336 may also collect liquid, such as exudate, from the tissue site 114 that is not absorbed by the microbial fuel cell 325. The second manifold layer 336 may also function to collect water as part of the cathode chamber of the microbial fuel cell 325 as described above. The second manifold layer 336 may have any size, shape, or thickness.

In one embodiment of the reduced pressure dressing 300; the liquid-air separator 340 may be a hydrophobic filter that inhibits or prevents passage of liquids through the liquid-air separator 340. Alternatively, the liquid-air separator 340 may be a gravity-based barrier system, or a device that includes a hydrophilic surface to encourage condensation or other separation of liquid from a fluid stream when the fluid stream passes over the surface. Other examples of liquid-air separators 340 may include sintered metals, sintered nylons, or any other material or device that is capable of separating liquid from a fluid stream, or that is otherwise capable of inhibiting or preventing the passage of liquid while allowing the passage of gases.

By restraining or preventing the flow of liquid, the liquid-air separator 340 prevents liquid from reaching the tubing adapter 120 or conduit 118 (see FIG. 1). By preventing liquid from reaching the conduit 118, the liquid-air separator 340 also prevents the liquid from reaching the reduced pressure source 134. The liquid-air separator 340 may prevent the passage of reduced pressure to the tissue site 114 when the liquid-air separator 340 becomes saturated, clogged, blocked, and/or wetted with liquid from the tissue site 114. The liquid-air separator 340 may also prevent the passage of reduced pressure to the tissue site 114 when a layer that abuts the liquid-air separator 340 becomes saturated with liquid. The presence of the diverter layer 332 between the liquid-air separator 340 and the microbial fuel cell 325 prolongs the period of time before the liquid-air separator 340 blocks the passage of reduced pressure.

The liquid-air separator 340 may have any size, shape, or thickness. In one example, the liquid-air separator 340 may be smaller than other layers in the reduced pressure dressing 300 due to cost considerations. The liquid-air separator 340 may also be wider than the tubing adapter 120 and an aperture 360 in the drape 128 so that liquid from the tissue site 114 cannot reach the tubing adapter 120 or the aperture 360.

Only a portion of the drape 128 is shown in FIG. 3 which may be larger or smaller depending on the configuration of the reduced pressure dressing 300. In one embodiment, the drape 128 may fully cover the multiple layers of the reduced pressure dressing 300. In this embodiment, the drape 128 may secure or assist in securing the reduced pressure dressing 300 to the tissue site 114 and in maintaining a seal around the tissue site 114. In this respect, both the drape 128 and the seal layer 322 may work together to create a seal around the tissue site 114. The drape 128 may also provide a protective barrier for the reduced pressure dressing 300 and the tissue site 114.

In the embodiment illustrated in FIG. 3, the drape 128 may cover and secure components and layers between the drape 128 and the diverter layer 332. In this embodiment, the drape 128 may be secured either adhesively or otherwise to the diverter layer 332. The diverter layer 332, which may be made from a similar material as the drape 128, is then secured to either or both of the seal layer 322 and the tissue at or near the tissue site 114. The diverter layer 332 in this embodiment secures and seals the components and layers beneath the diverter layer 332 at the tissue site 114.

In still another embodiment, the drape 128 may be designed such that the drape 128 will not adhere to wet surfaces, but will adhere to dry surfaces. Thus, when applying the drape 128, the drape 128 will not stick to moistened gloves or hands, thereby permitting easier handling of the drape 128 until the drape 128 is placed on a dry tissue site, such as a dry periwound area. The drape 128 may be any size, shape, or thickness. In one example, the drape 128 may be larger than any layer or components of the reduced pressure dressing 300. In another example, the size of the seal layer 322 may be larger than the size of the drape 128.

Reduced pressure may be applied to the plurality of layers of the reduced pressure dressing 300 via the aperture 360 in the drape 128. Although the aperture 360 is shown to be centrally located on the drape 128, the aperture 360 may be located anywhere on the drape 128 including a peripheral portion of the drape 128 that is adjacent to an edge of drape 128. Although the aperture 360 is shown to be circular, the aperture 360 may have any shape. In one example, the shape of the aperture is adapted to contour to one or more portions of the tubing adapter 120.

Although not shown in FIGS. 1 and 3, in one embodiment the reduced pressure dressing 300 may include an odor filter. The odor filter retains or prevents odor from exiting the reduced pressure dressing 300. The odor filter may be a carbon odor filter, which may include charcoal. In one example, the odor filter is a charcoal cloth. The odor filter may be positioned anywhere in the reduced pressure dressing 300 such as, for example, between the drape 128 and the liquid-air separator 340.

Although the drape 128, the liquid-air separator 340, the manifolds 324 and 336, the diverter layer 332, the microbial fuel cell 325, the seal layer 322, and the interface layer 320 have substantially square shapes in FIG. 3, each of these components, as well as other layers disclosed herein with respect to other embodiments, may have any shape as required to provide adequate reduced pressure therapy to the tissue site 114. For example, these components and layers may be polygonal, rectangular, circular, ovular, an irregular shape, a customized shape, or any other shape.

The reduced pressure dressing 300 may further include electrical circuitry (not shown) to connect microbial fuel cell 325 to an electrical load for utilizing and/or storing the generated electricity. For instance, in some embodiments, microbial fuel cell 325 may be electrically connected to one or more sensors (not depicted), such as, but not limited to, a pressure sensor, incorporated into the reduced pressure dressing 300 for providing primary and/or backup power to the one or more sensors. Additionally, reduced pressure dressing 300 may include other circuitry and/or wiring for connecting the reduced pressure dressing 300 to the reduced pressure treatment unit 136 for conveying data relating to the one or more sensors to the reduced pressure treatment unit 136.

While the various layers of the reduced pressure dressing 300 have been described as being "adjacent" to other layers, the term "adjacent" may refer to the layers being immediately adjacent, or alternatively that the layers may be positioned with other intervening layers in between. The term "layer" generally refers to portions or regions of the dressing that have different material properties or functions than other portions or regions of the dressing (i.e. other layers). The term "layer" is not meant to be spatially limiting however. The properties and functions associated with a particular layer may be combined with the properties and functions of another layer such that a single layer having multiple and different properties and functions is created. More specifically, for example, two or more layers may be physically or chemically bonded or combined to create a single layer without affecting the original material properties or functions of the original components. Conversely, a particular layer of the dressings described herein may be broken into two or more layers that each have similar properties or functions. Some of the layers may be omitted in certain embodiments.

The dressing may be either manufactured with some or all of the layers affixed together, or the dressing system may be assembled immediately prior to, or during, placement on a wound site.

A method for providing reduced pressure treatment to a tissue site is further provided according to an illustrative embodiment. The method includes applying a reduced pressure to the tissue site. The method collects exudate drawn from the tissue site in a liquid collection chamber and exposes the exudate in the liquid collection chamber to a micro-organism to generate electricity. In some embodiments, the liquid collection chamber may be incorporated into a reduced pressure dressing as described in FIG. 3 and/or the liquid collection chamber may be in an external collection canister associated with a reduced pressure treatment system as depicted in FIG. 1. Alternatively, in some embodiments, the liquid collection chamber may be incorporated into a reduced pressure treatment unit such as the reduced pressure treatment unit 136 depicted in FIG. 1.

It will be appreciated that the illustrative embodiments described herein may be used with reduced pressure treatment systems of any type, shape, or size and similarly with canisters of any type, shape, or size. The location of the inlet, outlet, and liquid-air separator may also vary depending upon the particular canister design.

It should be apparent from the foregoing that an invention having significant advantages has been provided. While the invention is shown in only a few of its forms, it is not just limited but is susceptible to various changes and modifications without departing from the spirit thereof.

It will be understood that the benefits and advantages described above may relate to one embodiment or may relate to several embodiments. It will further be understood that reference to 'an' item refers to one or more of those items.

Where appropriate, aspects of any of the examples described above may be combined with aspects of any of the other examples described to form further examples having comparable or different properties and addressing the same or different problems.

The steps of the methods described herein may be carried out in any suitable order, or simultaneously where appropriate.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of this invention.

We claim:

1. A reduced pressure treatment system for applying reduced pressure to a tissue site, the reduced pressure treatment system comprising:
    a reduced pressure source for providing reduced pressure;
    a distribution manifold fluidly coupled to the reduced pressure source for receiving reduced pressure and adapted to be positioned at the tissue site to distribute the reduced pressure to the tissue site; and
    an energy production device contained in a reduced pressure dressing, the energy production device comprising:
        an anode chamber fluidly coupled between the reduced pressure source and the distribution manifold to collect liquids containing exudates from the tissue site in response to application of a reduced pressure, and having an anode and micro-organisms disposed therein,
        a cathode chamber containing a cathode, and
        a proton exchange membrane in electrochemical communication between the anode and the cathode to enable the generation of electricity using the exudates.

2. The reduced pressure system of claim 1, further comprising the reduced pressure dressing fluidly coupled between the distribution manifold and the reduced pressure source for collecting the exudates.

3. The reduced pressure treatment system of claim 1, wherein the energy production device comprises a microbial fuel cell having a manifold for collecting the exudates in response to the reduced pressure.

4. The reduced pressure treatment system of claim 1, further comprising a power storage means for storing the generated electricity.

5. The reduced pressure treatment system of claim 1, further comprising one or more sensors configured to monitor a function of the reduced pressure treatment system and wherein the generated electricity is used to power the one or more sensors.

6. An energy production device for collecting liquids from a tissue site in response to application of a reduced pressure to the tissue site and providing energy to an electrical load, comprising:
    an anode chamber fluidly coupled between a source of reduced pressure and a distribution manifold at the tissue site to draw liquid including exudates from the tissue site into the anode chamber, the anode chamber including an anode disposed therein, the anode chamber containing micro-organisms for consuming a substrate within the exudates to produce carbon dioxide, protons, and electrons;
    a cathode chamber including a cathode adapted to receive the electrons from the anode, the cathode chamber containing an electron acceptor capable of accepting the electrons from the cathode;
    a proton exchange membrane positioned between the anode and the cathode to enable the flow of the protons from the anode chamber to the cathode chamber; and
    an output electrically coupled to the anode and the cathode for providing the energy to an electrical load in response to the microbial production of energy from the exudates;
    wherein the anode, the cathode, and the proton exchange membrane are housed in a reduced pressure dressing.

7. The energy production device of claim 6, wherein the anode chamber includes a manifold for collecting the liquid in response to the reduced pressure.

8. The energy production device of claim 6, wherein the cathode chamber includes a manifold for containing the electron acceptor.

9. The energy production device of claim 6, wherein the anode chamber includes a manifold for collecting the liquid in response to the reduced pressure.

10. The energy production device of claim 6, wherein the cathode chamber includes a manifold for containing the electron acceptor.

11. A method for providing reduced pressure treatment to a tissue site, the method comprising:
    applying a reduced pressure to the tissue site;

collecting exudate drawn from the tissue site in an anode chamber incorporated in a reduced pressure dressing and having an anode and micro-organisms disposed therein, the anode chamber separated from a cathode chamber by a proton exchange membrane in electrochemical communication with a cathode disposed in the cathode chamber; and utilizing the exudate in the anode chamber to generate electricity.

12. The method of claim 11, further comprising powering an electrical load using the electricity generated from the exudate.

13. The method of claim 12, wherein the electrical load is a reduced pressure source that is configured to provide the reduced pressure.

14. The method of claim 12, wherein the electrical load is a sensor incorporated in a reduced pressure treatment system.

15. The method of claim 14, wherein the sensor is a pressure sensor.

16. The method of claim 14, wherein the sensor is a pH sensor.

17. The method of claim 11, further comprising using the generated electricity to power one or more components of a reduced pressure treatment system.

18. The method of claim 11, further comprising storing the generated electricity.

19. The method of claim 11, further comprising utilizing the generated electricity to recharge a battery of a reduced pressure treatment system.

20. The method of claim 11, further comprising utilizing a second power source in conjunction with the generated electricity to power one or more components of a reduced pressure treatment system.

21. The method of claim 11, further comprising using the generated electricity to power an external component of a reduced pressure treatment system.

22. The method of claim 11, further comprising using the generated electricity to power circuitry for relaying data related to one or more sensors associated with a reduced pressure treatment system to a monitoring device.

23. A method of generating electricity, comprising the steps of applying a reduced pressure to a tissue site of a patient to extract wound exudate;

collecting the exudate in an anode chamber having an anode, the anode chamber contained in a reduced pressure dressing;

consuming a portion of the exudate using micro-organisms to create protons and electrons; and generating electricity from flow of the protons through a proton exchange member to a cathode chamber to combine with electrons from a cathode in the cathode chamber, which cathode is electrically connected to the anode through a circuit to be powered.

* * * * *